United States Patent [19]
Hughes, Jr. et al.

[11] Patent Number: 5,264,208
[45] Date of Patent: Nov. 23, 1993

[54] POTENTIATION OF TUMOR NECROSIS FACTOR (TNF) OF INTERFERON B1 (IFN-B1) ANTIVIRAL ACTIVITIES BY AN ANTI-CACHEXIA AGENT

[75] Inventors: Thomas K. Hughes, Jr.; Charlotte S. Larned, both of Galveston, Tex.

[73] Assignee: Board of Regents The University of Texas System

[21] Appl. No.: 473,271

[22] Filed: Jan. 31, 1990

[51] Int. Cl.$^5$ ................... A61K 37/66; A61K 45/05
[52] U.S. Cl. ................... 424/85.1; 424/85.4
[58] Field of Search ................... 424/85.1, 85.4

[56] References Cited

U.S. PATENT DOCUMENTS 4,650,674  3/1987  Aggarwal et al. ................... 424/85

OTHER PUBLICATIONS

Hughes, et al., 1989, "Modulation of Tumor Necrosis factor activities . . . ", Int. J. Immunopharmac. 11(5):501–507.
Moritz, et al., 1989, "Phase I study of recombinant human tumor . . . " Cancer Immunol. Immumother. 29:144–150.
Lenk, et al., 1989, "Phase II clinical trial of high-dose . . . " Cancer Chemotherapy and Pharmacology 24:391–392.
Chlebowski, et al. "Hydrazine sulfate in cancer patients . . . " Cancer 59:406–410, 1987.
Sulis, et al., 1989, "Intralymphatic infusion of interferon . . . " Cancer Chemo. and Pharm. 24:393–394.
Baron, et al., 1987 (eds) In: "The Interferon System . . . " A Current Review pp. 2–17.
Aggarwal et al. (1985) Methods in Enzymology, 116:448–457.
Klostergaard et al. (1985) Biological Abstracts, 80(5): Abstract 40216, p. AB–403.
Klostergaard et al. (1987) Chemical Abstracts, 106(25): Abstract 212340T, p. 521.
Klostergaard et al. (1987) Chemical Abstracts, 106(13): Abstract 100662T, p. 517.
Klostergaard, J. (1987) *Lymphokine Research*, 6:19–28.
Klostergaard et al. (1987) Cancer Res., 47:2014–2019.
Klostergaard et al. (1985) Journal of Biological Response Modifiers, 4:195–209.
Klostergaard et al. (1987) Journal of Biological Response Modifiers, 6:313–330.
Lane et al. (1990) Annals of Internal Medicine, 112(11):805–811.
Saah et al. (1987) J. Clin. Microbiol., 25(9):1605.
*Molecular Biology of the Cell*, (2nd ed. 1989), Alberts et al., eds.: p. 251, p. 1204.
Mestan et al. (1986), Nature, 323: 816–819.
G. Semenzato (1990), Brit. J. Cancer 61 (3):354–361.
Stewart, William E., II, (ed) (1979), In: The Interferon System pp. 200–222.
Hughes, et al., (Feb. 9, 1989), FASEB Journal, 3(3):A636.
Babich, et al., (1989), Carcinogenesis, 10(2):265–8.
Silverstein, et al., (1989), Immunopharmacology, 17:37–43.
Gold, (1986), Proc. Annu. Meet. Am. Assoc. Cancer Res., 27:279.
Kim, et al., (1989), Proc. Annu. Meet. Am. Assoc. Cancer Res., 30:A1618.
Gold, et al., (1987), Nutr. Cancer, 9(2–3):59–66.
Dialog search.
Sonnenfeld, et al., (1983), Cancer Res., 43(10):4720–2.
Lahdevirta, et al., (1988), Am J. Med., 85(3):289–91.
Gold, (1989), Proc. Annu. Meet. Am. Assoc. Cancer Res., 30:A2164.
Gold, (1989), Proc. Annu. Meet. Am. Assoc. Cancer Res., 29:A1296.
Stovroff, et al., (1989), J. Surg. Res., 46(5):462–9.
Stovroff, et al., (1989), Arch Surg., 124(1):94–9.

Primary Examiner—Christine M. Nucker
Assistant Examiner—Lynette F. Smith
Attorney, Agent, or Firm—Arnold, White & Durkee

[57] ABSTRACT

The present invention discloses the use of a anti-cachexia agent with an antiviral agent, preferably used as a therapeutic agent in the treatment of viral infections. The anti-cachexia agent acts to potentiate the antiviral activity of the antiviral agent as much as several hundred fold. The anti-cachexia agent also acts to decrease, or halt the anti-proliferative or host destroying activities of the antiviral agent. The most preferred anti-cachexia agent of the present invention is hydrazine sulfate. The most preferred antiviral agent of the present invention is interferon, tumor necrosis factor or any combination thereof.

8 Claims, 2 Drawing Sheets

HS 0 ug/ml
HS 100 ug/ml
HS 30 ug/ml

POTENTIATION OF TUMOR NECROSIS FACTOR (TNF) OF INTERFERON B1 (IFN-B1) ANTIVIRAL ACTIVITIES BY AN ANTI-CACHEXIA AGENT

BACKGROUND OF THE INVENTION

1. Field of the Invention

The present invention relates to the field of antiviral agents, and more specifically to their use in conjunction with known anti-cachexia agents. More particularly, the present invention relates to the potentiation of the antiviral activity of an antiviral agent (i.e., interferon or tumor necrosis factor) with an anti-cachexia agent (hydrazine sulfate) both in vitro and in vivo.

The present invention also relates to therapeutic treatments for the clinical management of viral infections. Methods for enhancing the in vivo antiviral activity of such agents as tumor necrosis factor and interferon are also included. Methods for preparing a therapeutic agent for the treatment of viral infections are also described.

2. Description of the Related Art

The behavior of tumor viruses both in vitro and in vivo[40] has been studied in efforts to define the biology and molecular biology of cell transformation. Several types of tumor viruses, defined as viruses which have the ability to induce tumors experimentally in laboratory animals or to transform cells that are maintained in culture,[27] have been linked as the causative agents of different cancers (Adenovirus (Ad12 and Ad18)) and herpesvirus infections (HSV-1 and HSV-2).

Research in the field of tumor and virus biology has provided critical insights regarding substances which affect their pathology. Two substances which appear to play important roles in tumor and viral growth and replication are tumor necrosis factor (TNF) and interferon (IFN).

Information gathered regarding tumor necrosis factor (TNF) and interferon (IFN) suggest they individually possess antiviral activity, making them potential candidates in the treatment of viral infections and tumors. However, serious side affects attendant treatment with therapeutically valuable doses of TNF or IFN limit their clinical usefulness. Thus, the employ of these agents in combating cancers and viral tumors has met with, at best, marginal success.

Additionally, it has been observed that patients with cancerous conditions typically suffer unexplained weight loss that is not controlled by antiviral agent treatments. This unexplained weight loss, or cachexia, is also a condition attendant several lethal viral infections, the most notorious of these being the HIV-induced infections (i.e., AIDS, ARC). Abnormal carbohydrate metabolism, as evident from changes in glucose production and glucose tolerance, has been cited as perhaps the precipitating condition facilitating this cachexia in cancer patients.[41]

Tumor necrosis factor (TNF) has been shown to be produced by monocyte/macrophages in response to endotoxin and other stimuli. TNF has now been shown to have a plethora of activities, which include antiviral activity,[1] potentiation of interferon's antiviral activity,[2] enhancement of monocyte motility,[3] and activation of monocyte/macrophage cytotoxic activities.[4]

TNF has also been shown to be identical to a known mediator of tissue wasting in neoplastic states,[5] cachectin. TNF, like cachectin, is also known to promote tissue wasting processes. This wasting process greatly accelerates the morbidity and mortality of affected individuals. The mechanisms by which TNF/cachectin exert their effects are not entirely known, but it has been suggested that they are mediated by the suppression of lipoprotein lipase activity.[6] Serum cachectin levels have been directly correlated with tumor burden in sarcoma bearing experimental animals, and inversely with food intake and body weight.[7] Elevated levels of cachectin/TNF have also been associated with HIV-infected persons with AIDS or ARC, but not in asymtomatic HIV-infected persons.[8]

Unfortunately, treatments with high dosages of tumor necrosis factor alone have been associated with such side affects as hypotension, leukocytosis, fever, chills, neurotoxicity, nausea and vomiting.[29] Moreover, high doses of IFN alone to cancer patients have been reported to demonstrate no therapeutic value.[29] These side affects are very similar, but more rapid, in onset than those observed with other biological response modifiers such as endotoxin and the interleukins.

Thus, the side affects of TNF has limited its use as an antiviral agent, despite its known antiviral activities, in addition to its host-destroying effects. It is uncertain, but these studies suggest tumor necrosis factor (TNF) may have intrinsic antiviral activity, as well as having the ability to potentiate the antiviral activity of interferon.

The interferons comprises a family of 20 to 25 low-molecular-weight proteins which cause cells to become resistant to the growth of a wide variety of viruses. The interferons can be divided into three species: IFN-alpha, IFN-beta, and IFN-gamma. The interferons differ in the agent which induces them and in the cell type which produces them.

Human IFN-alpha is produced by lymphocytes and macrophages which have been induced with components of foreign cells, and perhaps cells made foreign by transformation, infection and certain chemicals. Genetic sequences for at least 17 different IFN-alpha subtypes are encoded in human DNA. At least 8 are naturally expressed. The genes for IFN-alpha are all located in one region of human chromosome 9. IFN-alpha molecules are believed to be comprised of about 165–166 amino acids.

Human IFN-beta is produced by fibroblast and epithelial cells which have been induced with foreign nucleic acids. Genetic sequences for at least two IFN-beta subtypes are encoded in the DNA of humans. Both are expressed naturally. The gene for one of the IFN-beta subtypes has been mapped. It is located in close proximity to the IFN-alpha gene on human chromosome 9. The mature IFN-beta molecules are composed of about 166 amino acids. The two beta interferon subtypes, $B_1$ and $B_2$, also differ greatly in their activity. For example, interferon $B_1$ has been found to have antiviral activity, while interferon $B_2$ (alias interleukin-6)[42] does not have such antiviral activity. It should be noted that in the mouse system, IFNs alpha and beta are often produced concurrently.

IFN-gamma is produced by T-lymphocytes which have been stimulated with foreign antigens to which they have been previously sensitized, or with mitogens which stimulate this induction. Only one genetic sequence from IFN-gamma has been identified in the DNA of man. It is located on human chromosome 12.

IFN-gamma molecules are composed of 146 amino acids but processing may alter this number.

As noted, interferon $B_1$ is known to have antiviral activity. However, none of the interferons, to the Applicants' knowledge, have been associated with tissue-wasting or cachexia. The interferons were first recognized for their extraordinarily potent antiviral properties, and it has now been established that they may profoundly affect other viral, cellular and bodily functions, including cell metabolism and growth, immunity and tumor growth. Recent studies also demonstrate that interferons potentiate the cytotoxic effects of certain anti-neoplastic drugs on human tumor cells both in vitro and in vivo. However, the mechanism of interferon's synergistic action remains unknown.[28] Additionally, there is no clear-cut evidence that TNF is effective in the clinical setting.

Unfortunately, the interferons have been found to cause some undesirable side affects in vivo, such as fever, bone marrow suppression, fatigue, hypertension, malaise, nausea, anorexia, myalgia tachycardia, and impaired liver functions.[9, 29] Additionally, alpha-interferon, but not the other two classes of interferons, binds to opiate receptors in vitro, and causes endorphin-like opioid effects in vivo, including analgesia, lack of spontaneous locomotion, and catalepsy.[32]

These prior studies, along with others[9] establish that interferon is a useful therapy for particular conditions, particularly in cancer therapy, but cannot be used alone as a complete treatment regimen. Interferons (IFNs) have been tested in combination with other antitumor drugs in an effort to enhance antiviral activity and to reduce side effects associated with cancer chemotherapy. However, such has met with highly inconsistent results.[33, 34]

One agent, hydrazine sulfate, has been identified as a potential therapeutic drug to treat the unexplained weight loss observed in cancer patients.[37] In particular, hydrazine sulfate has been shown to alter the abnormal carbohydrate metabolism described in the literature in cancer patients. (Id.) The potential of HS as an anti-cachexia agent is recognized as a consequence of its ability to inhibit gluconeogenesis, and particularly, the enzyme phosphoenolpyruvate carboxykinase.[10]

Recently, hydrazine sulfate has been shown to influence whole body protein turnover in cancer patients.[37] The reduction in host weight loss (i.e., tissue wasting) exhibited in cancer and other tumor-bearing patients treated with hydrazine sulfate is described as a result of its effect on gluconeogenesis in the animal.[35] Additionally, hydrazine sulfate has little direct antiviral activity at low doses or at high doses to the Applicants, knowledge. Pretreatment with hydrazine sulfate has also been shown to protect against lethality after endotoxin challenge.[38]

The use of hydrazine sulfate as an anticancer agent, in combination with another agent to enhance or potentiate its anticachexia affects has been considered by others. For example, the use of vitamin $K_2$ or $K_3$ (menadione) has been shown to synergize and/or potentiate the antitumor effect of hydrazine sulfate, while at the same time minimizing host toxicity (i.e., weight loss) and its symptomatically attendant tumorous conditions.[11, 12]

It has been reported that hydrazine sulfate (HS), a non-competitive inhibitor of phosphoenolpyruvate carboxykinase in gluconeogenesis, can inhibit the wasting process in cancer patients.[10, 13] It was hypothesized that increased levels of lactic acid derived from highly glycolytic neoplastic tissue, amino acids from peripherial protein breakdown, and glycerol from lipid mobilization, contributed to the development of a greater than normal gluconeogenic pathway. This in turn resulted in greater amounts of energy being lost from normal host tissue to contribute to the obligatory production of glucose; hence, the wasting process. However, the possibility exists that HS might also be playing a role by inhibiting TNF/cachectin by some as yet undefined mechanism.

Some studies suggest that hydrazine sulfate as a component of tobacco smoke may be important in inhibiting interferon induction.[14] However, this affect was exhibited at only one 24 hour post-treatment time, with no affect being exhibited at any of the other treatment times examined.[14] While hydrazine sulfate has been shown to induce tumor regression and to inhibit tumor growth at 24 hours pretreatment, it has not as yet been shown to directly or indirectly inhibit TNF cytolytic activity or to potentiate TNF antiviral activity.

A combination therapeutic agent aimed at reducing the cytolytic action of these and other antiviral agents has not yet been examined. Moreover, the role of interferon in the management of various diseases has not yet been fully established.

Some investigators have examined the affect of administering TNF with such substances as adriamycin, a chemotherapeutic agent known to have antitumorigenic effects.[15] These particular studies found a synergistic enhancement of the adriamycin cytotoxicity in vitro, and further described a protective effect against host cachexia in vivo in animals treated with this combination.[15] However, no affect was described in regard to antiviral activity with this combination. Thus, the relatively high doses of TNF used thus far to elicit antiviral activity in an animal continues to limit the clinical utility of interferon owing to the undesirable side effects attendant these doses.

A combination therapeutic agent remains to be formulated which would enhance the antiviral activity of an antiviral agent to a level that would allow a reduction in currently used doses, thus minimizing the many in vivo side effects which have limited its clinical application. Ideally, such a combination would synergistically enhance the antiviral activity of the antiviral agent, and provide a protective function to the infected animal against continued host wasting (i.e. loss of host cell function and from the destruction of normal host cell integrity). Such an combination would present a significant advance in the clinical management of patients with viral and tumorous conditions, and presents a possible solution to the treatment of HIV infections such as AIDS, AIDS-related conditions and other viral infections, while halting the exacerbating and symptomatic tissue wasting attendant many virally-induced conditions.

SUMMARY OF THE INVENTION

The present invention presents the surprising discovery that hydrazine sulfate significantly inhibits the cytolytic activity of tumor necrosis factor (TNF) in a dose-dependent fashion. Moreover, this surprising hydrazine sulfate-induced protective effect has been found to be stable to washing of cells in vitro. In addition to hydrazine sulfate's effect on TNF's cytolytic activity, Applicants have discovered the unexpected and further surprising ability of hydrazine sulfate to synergistically potentiate TNFs antiviral activity up to several hundred fold. This potentiation of antiviral activity may more specifically exist between hydrazine sulfate and interferon, most preferably TNF-induced interferon $B_1$.

Implementing the above surprising and unexpected interactions between hydrazine sulfate (an anticachexia agent), TNF, and/or interferon (antiviral agents), the present invention includes a composition of matter comprising an antiviral agent together with an anticachexia agent capable of potentiating the antiviral activity of the antiviral agent. This composition preferably comprises a therapeutic agent, wherein the antiviral agent in one particularly preferred embodiment comprises interferon (IFN) and tumor necrosis factor (TNF). In still another embodiment of the invention, the antiviral agent preferably comprises interferon or tumor necrosis factor.

Any physiologically acceptable, non-toxic anticachexia agent which potentiates the antiviral activity of an antiviral agent (such as tumor necrosis factor (TNF) or interferon (INF)) may be used in the therapeutic agent defined in the present invention. A particularly preferred anticachexia agent comprises hydrazine sulfate. Preferred concentrations of hydrazine sulfate in the claimed compositions are those amounts which elicit a decrease in host wasting. More particularly, host wasting refers to, by way of example, a decrease in body weight. Host tissue wasting is an often attendant symptom of some viral infections. For example, viral infections such as AIDS, and the various forms of cancer, are frequently accompanied by host weight loss.

In these particular therapeutic compositions, the antiviral activity of interferon, most particularly interferon $B_1$, and tumor necrosis factor has surprisingly been found to be synergistically potentiated by its coadministration with hydrazine sulfate in vitro.

Additionally, the cytolytic or tissue wasting effects of TNF are unexpectedly and surprisingly shown to be reduced or inhibited when administered together with hydrazine sulfate in vitro. This particular effect has advantageously been shown to exist without a concomitant reduction in the potentiated antiviral activity of the antiviral agent.

It is known that hydrazine sulfate alone provides an anticachetic protection against host cell wasting in vivo. It has also been established that tumor necrosis factor possesses cytolytic activity. Given the data thus far collected, and the established effect of HS alone in vivo, it is postulated that the inhibition of TNF cytolytic activity by hydrazine sulfate demonstrated in vitro may also exists in vivo. Thus, the present invention also comprises a method of treating a viral infection in an animal while arresting cytolytic destruction of host tissues through concomitant administration of hydrazine sulfate with interferon or tumor necrosis factor.

While the therapeutic agent of the present invention includes any anticachexia agent which potentiates the antiviral activity of tumor necrosis factor (TNF) or interferon (INF), a particularly preferred anticachexia agent is hydrazine sulfate. Other anti-cachexia agents may include non-toxic derivatives of hydrazine and hydrazine sulfate, as well as other anticachectic agents. One skilled in the art may find these anti-cachexia agents suitable when used in conjunction with the antiviral agents described in the practice of the present invention.

Particularly preferred antiviral agents of the described treatments of the present invention comprise tumor necrosis factor (TNF) and interferon (IFN) together with hydrazine sulfate. Alternatively, the therapeutic agent comprises either interferon (IFN) or tumor necrosis factor (TNF) together with hydrazine sulfate. Preferred embodiments of the particular therapeutic combinations described, therefore, include tumor necrosis factor and hydrazine sulfate or interferon and hydrazine sulfate.

While any of a number of the family of interferons (except interferon $B_2$) may comprise the antiviral agent of the present invention, those interferons most preferred include interferon $B_1$, interferon alpha or interferon gamma, or a mixture thereof. Interferon $B_2$ would not be expected to be effective in the present compositions, as this particular interferon has been demonstrated to be essentially incapable of inducing an antiviral state and is thus poorly antiviral.

The interferon included in the described compositions and therapeutic agents may be either that interferon naturally occurring or interferon produced through recombinant techniques (rIFN). The preparations of rIFN are well known to those skilled in the art of molecular biology.

The effective dosages of interferon in the therapeutic agent will vary depending on the kind of interferon used (i.e., natural or recombinant) as well as the mode by which the particular interferon is administered to the animal (i.e., I.V., I.M., I.P.). Natural HuIFN-alpha or -beta has been administered at doses of $3-20 \times 10^6$ IU, but mainly at $3-10 \times 10^6$ IU; recombinant HuIFN-alpha, at doses of $3-100 \times 10^6$ IU, mainly at $3-20 \times 10^6$ IU in humans. The antiviral agent HuIFN-alpha has mainly been administered I.M., while HuIFN-beta has been administered through an intravenous injection because no or low IFN-activity has been detected in the serum of the patients when HuIFN-beta was injected intramuscularly (IM). Interferon-alpha is most preferable administered by intramuscular (I.M.) injection. For a review of interferon effects alone in vivo, see *The Interferon System, A Current Review to* 1987 (Baron et al., eds.), 1987.

As will be appreciated, calculation of the dose or treatment amount or concentration of TNF or IFN to be administered will vary according to the specific activity of the particular preparation of IFN or TNF. The specific activity of a preparation will vary according to the purity of each undiluted preparation, and is calculated as a function of "units" per mg of protein.

The present invention also includes methods of treating a viral infection in an animal. This method of treatment comprises several steps. Initially, the method calls for the identification of an animal having a viral infection. After identifying the animal, the method calls for administering to the animal a viral-inhibiting amount of a therapeutic agent comprising an antiviral agent together with an anticachexia agent which potentiates antiviral activity of the antiviral agent being administered. The particular antiviral agents in a particularly preferred embodiment are interferon and tumor necrosis factor. The antiviral agent may comprise either a combination of interferon and tumor necrosis factor, or either one of these agents individually. The method in a particularly preferred embodiment employs a therapeutic agent which comprises an anticachexia agent further defined as hydrazine sulfate.

The therapeutic agent is to be administered in a pharmaceutically acceptable viral-inhibiting concentration, which is defined herein as a pharmaceutically acceptable concentration or a dose sufficient to inhibit viral replication. The inhibition of viral replication may be indicated by a complete remission (CR) or partial remission (PR) of the particular disease or by subsidence of viral symptoms in the patient. Remission is to be measured as an absence (CR) or more than 50% reduction (PR) of the virus in the infiltrate of body samples, such as in bone marrow aspirates and biopsies. The method next calls for monitoring the animal for systemic antiviral responses and then discontinuing administration of the therapeutic agent upon the subsidence of the viral infection. Subsidance of the viral infection is indicated by the reduction or elimination of circulating virus in an animal, which may be assessed through the analysis of a biological sample from the patient. Subsidance of viral infection may also be indicated by the subsidance of any of the viral infections symptoms in the patient.

For purposes of the presently described methods, an antiviral response is defined as a subsidence or elimination of viral infection symptoms. By way of example, viral infection symptoms include elevated levels of circulating virus in the infected animal, weight loss, tumor growth, chills, fever, headache, nausea, as well as a variety of other flu-like symptoms.

A particularly preferred application of the present invention includes a method of inhibiting cytolytic activity of tumor necrosis factor comprising administering hydrazine sulfate therewith. Use of the claimed invention in vitro has been found in a preferred embodiment to comprise hydrazine sulfate at a concentration of about 30 to about 300 ug/ml of the culture media. A more preferred range of included hydrazine sulfate in vitro is between about 30 to about 100 ug/ml of the culture media. In an even more preferred embodiment, hydrazine sulfate is to be included at a concentration of between about 50 to 80 ug/ml of the culture media. In a most preferred embodiment, the concentration of hydrazine sulfate is about 60 ug/ml of the culture media.

In a further embodiment of the invention, hydrazine sulfate is included at a concentration of about 60 ug/ml with tumor necrosis factor to effect the enhanced antiviral effects and cell-protective effects of the present invention in vitro.

Tumor necrosis factor (TNF) activity is measured in lytic units. Thus, proposed doses of TNF, as well as other antiviral agents of the present invention, will be assessed in lytic units (u/ml) for in vitro use, and TNF and IFN are to be expressed in units/m$^2$, or U/m$^2$ for in vivo use. Cytolytic activity was assessed per lytic unit, which is the amount of TNF that causes lysis of 50% of 50,000 mouse L-929 cells that have been treated with 5 ug/ml of actinomycin D. Actinomycin enhances the sensitivity of cells to the cytolytic effects of tumor necrosis factor. Interferon has no cytolytic activity. The length of the assay for the measurement of cytolytic activity is about 24 hours.

Antiviral activity was measured in vitro using HEp-2 cells which had been pretreated with TNF or IFN. HEp-2 cells were infected with VSV at a multiplicity of infection of 0.5 and then the virus was harvested. These virus particles were then used in a modified plaque reduction assay on L-929 cells to determine virus yields.

Proposed In Vivo Use

It is hypothesized that administration of hydrazine sulfate at a dose of between 60 mg and 250 mg per day would be effective in eliciting a host protective effect against tissue wasting (cachexia) of normal tissues and in potentiating the antiviral activity to kill the virus of the particular antiviral agent employed.

In a particularly preferred embodiment for in vivo use, hydrazine sulfate is administered at a dose of between 60 mg and 250 mg per day. Most preferably, the dose of hydrazine sulfate is between about 100 mg and 200 mg per day. In an even more preferred embodiment of the present invention, the dose of hydrazine sulfate expected to be an effective host-protective dose is about 180 mg per day. The therapeutic agent in on particularly preferred embodiment comprises hydrazine sulfate with the particular antiviral agent, tumor necrosis factor.

In one embodiment of the present invention, the method of treating a viral infection in an animal, such as a human, comprises administering a therapeutic agent which is postulated to preferably comprise a daily dose of between about $10 \times 10^5$ U/m$^2$ to $20 \times 10^5$ U/m$^2$ TNF with between about 100 and 200 mg hydrazine sulfate. Most preferably, the daily dose of hydrazine sulfate comprises about 180 mg.

In another embodiment of the described method, the therapeutic agent is defined further as comprising about $15 \times 10^5$ U/m$^2$ TNF per 100 mg hydrazine sulfate administered per day. In one particularly preferred treatment regimen, the above amounts of TNF and HS are administered either daily, but may instead comprise other treatment schedules as may be clinically indicated. Treatment regimens are expected to comprise a period of between about 30 and 90 days, but may be longer or shorter depending upon when symptoms of the condition subside.

The preferred dosages of TNF, as expressed in mg/m$^2$, are postulated to be between 0.04 mg/m$^2$ to 0.20 mg/m$^2$. Most preferably, the dose of TNF expected to be effective as an antiviral agent as potentiated by hydrazine sulfate in vivo is between 0.06 mg/m$^2$ to 0.16 mg/m$^2$. The most preferred dose of TNF is expected to be about 0.10 mg/m$^2$ in vivo when administered with hydrazine sulfate. Most preferably, hydrazine sulfate is to be administered at a dose of 180 mg per day with the above ranges of TNF per day.

Use of the present therapeutic agent in the treatment of cancer patients is anticipated as requiring a regimen of daily or thrice weekly treatment, or as may be otherwise clinically indicated, for at least 6 months. An extended treatment regimen has been found to render a lesser incidence of relapse in patients with hematologic cancer treated with interferon-alpha alone(p. 488).[9]

The present methods define treatments for IFN sensitive or TNF sensitive viral infections. While any of such viral infections is contemplated as treatable with the present methods, those in which the human immunodeficiency virus (HIV) is the causative agent are particularly envisioned. By way of example, such viral infections include acquired immunodeficiency syndrome (AIDS), ARC, and other HIV-linked conditions.

Exact effective doses of hydrazine sulfate in vivo to be used together with particular antiviral agents are yet to be ascertained.

The invention also includes a method of preparing a therapeutic agent for treatment of viral infections. This method comprises preparing a solution of hydrazine sulfate to form a stock solution A; sterilizing the stock solution A; preparing a sterile solution of interferon or tumor necrosis factor to form a stock solution B; and diluting the stock solution A and the stock solution B to a pharmaceutically acceptable final concentration to form a therapeutic agent for the in vivo treatment of viral infections.

For in vitro use, the stock solution A comprises hydrazine sulfate at a concentration of about 25 mg/ml in a pharmacologically acceptable solution, such as phosphate buffered saline or a cell culture medium. In a most preferred embodiment for in vitro use, the stock solution A (hydrazine sulfate) is diluted to a concentration of 100 ug/ml in phosphate buffered saline. Additionally, the stock solution B (interferon and/or tumor necrosis factor) is preferably diluted so as to achieve a concentration capable of exhibiting 100 lytic units/ml. for in vitro use. In still another preferred embodiment of the invention, the stock solution B comprises interferon at a concentration of about 25 mg/ml.

These concentrated stock solutions are even more fully described below:

Stock solution A: HS—For in vitro use, HS is prepared as stock solution of 25 mg/m$^1$ hydrazine sulfate in phosphate buffered saline or cell culture medium. The pH is then neutralized with NaOH. The solution A is then filter sterilized and diluted to a desired concentration for administration in test culture. For in vivo use, HS may be administered in tablet form so as to achieve the preferred daily doses of HS described above.

Stock solution B: For in vitro use, TNF and IFN are to be diluted in the same diluent as the hydrazine sulfate, (i.e. cell culture medium or phosphate buffered saline). Where both interferon and tumor necrosis factor are used together, the final appropriate concentrations are arrived at when the two solutions (i.e., TNF and IFN) are mixed together.

Where the interferon or tumor necrosis factor was used in vitro, the stock solution is diluted so as to achieve a concentration expressed as U/ml. A stock of TNF was prepared at 100 U/ml. Thus, 1 ml of TNF stock was added for every 9 ml of culture media when studies for in vitro affects were conducted. This stock was diluted accordingly to achieve concentrations of TNF of 30 U/ml culture media and 10 U/ml culture media.

Where the interferon or tumor necrosis factor is to be employed in vivo, the stock solution is diluted to achieve a concentration expressed as U/m$^2$ (units/body square meter) or mg/m$^2$ (mg/body square meter). It is postulated that relatively low concentrations of TNF and/or IFN will provide the antiviral effect of the claimed invention in vivo. In this regard, ranges of TNF concentration should be between 0.04 mg/m$^2$ to 0.28 mg/m$^2$ for human use, as extrapolated from Moritz, et al.'s clinical studies of TNF alone[39]. Levels of IFN expected to provide the antiviral affect of the present invention were extrapolated from Imanishi et al.'s clinical studies of IFN alone.[9]

As noted, the lytic activity of a solution of TNF or interferon may vary from batch to batch. Use of the described L-929 cytotoxicity assay may be employed by those skilled in the art to determine the particular lytic unit activity in the preparation used.

Insofar as the present invention concerns a method of treating a viral infection in an animal, the method comprises, in addition to the methods above, a method for potentiating antiviral activity of tumor necrosis factor. Applicants postulate the enhancement of antiviral activity in tumor necrosis factor used in conjunction with hydrazine sulfate will be mirrored in vivo. Exact doses for in vivo application of the present invention await further dose studies. The method of potentiating antiviral activity of tumor necrosis factor comprises administering hydrazine sulfate concurrently or prior to TNF or interferon administration.

Applicants have found that the host-protective effect of hydrazine sulfate is most pronounced in vitro where a cell culture is exposed to hydrazine sulfate prior to exposure to tumor necrosis factor. Thus, when the potentiation of the antiviral activity of tumor necrosis factor or interferon in vitro is the object of the invention, hydrazine sulfate is to be administered at least 1 hour prior to exposure to tumor necrosis factor. More preferably, hydrazine sulfate is to be administered between about 4-8 hours prior to exposure to tumor necrosis factor. In a most preferred embodiment, the hydrazine sulfate is to be administered about 8 hours prior to exposure of the culture to tumor necrosis factor.

In the above described methods for potentiating antiviral activity, the antiviral agent most preferred is tumor necrosis factor. More particularly, an in vitro dose of as little as about 30 ug/m$^1$ hydrazine sulfate has been found to potentiate the antiviral activity in about 1000 lytic units/ml of tumor necrosis factor. Applicants have found that the administration of about 30 ug/ml hydrazine sulfate potentiates the antiviral activity of TNF several hundred fold in some cases. More particularly, the administration of 30 ug/ml hydrazine sulfate prior to the administration of about 100 lytic units tumor necrosis factor potentiated the antiviral activity of tumor necrosis factor over 100 fold (about 170 fold) in vitro (See Table 1).

Insofar as the present invention comprises potentiating the antiviral activity of tumor necrosis factor in vitro, the invention further comprises a method for inhibiting the cytolytic activity of an antiviral agent, such as tumor necrosis factor, in vitro.

The protective effect of HS is expected to counteract the antiproliferative (i.e., cytolytic) activities demonstrated by TNF in vitro.

The method in a particularly preferred embodiment for the inhibition of cytolytic activity by tumor necrosis factor in vitro, includes pretreatment of the cell culture with hydrazine sulfate 2-4 hours prior to exposure to tumor necrosis factor. Most preferably, the hydrazine sulfate is administered to the cell culture 4 hours prior to exposure to tumor necrosis factor. It has been found that the above in vitro effects are demonstrated with particularly preferred concentrations of hydrazine sulfate. Specifically, the method provides for the administration of about 100 ug/m$^1$ hydrazine sulfate to protect against the cytolytic activity of about 30 lytic units/ml tumor necrosis factor in vitro. Optionally, in a most preferred embodiment, hydrazine sulfate is to be administered in vitro about 4 hours prior to exposure to tumor necrosis factor.

Applicants have correlated the observed in vitro cytolytic activity to the observed viral-linked in vivo tissue wasting or cachexia, insofar as these two activities involve anti-proliferation of cells and/or cell destruction. Applicants postulate the in vivo use of hydrazine sulfate together with tumor necrosis factor in the treatment of viral infection will enhance the antiviral action while suppressing the cytolytic action of tumor necrosis factor. Thus, an object of the present invention is the development of a therapeutic agent which is effective to both arrest viral replication (enhance antiviral activity) while simultaneously retarding tissue wasting (cytolytic activity) in normal host tissues.

Use as A Therapeutic Agent—Proposed Use in Humans

It is contemplated that the described therapeutic agent would be useful in the treatment of a variety of viral infections in humans. The therapeutic agent may be administered through a variety of routes, including intramuscular (IM) or intravenous (IV) injection, as drops or by intralesional injection.

Where the antiviral agent includes interferon in addition to or in place of TNF, the mode of administration will also depend on the particular type of interferon administered. Prior studies suggest that the effectiveness of the interferon in vivo varies depending upon the mode of administration.[9]

A particular dosage regimen hypothesized as effective for the treatment of viral infections in humans is the prescribed therapeutic agent administered between 1 to 5 days a week, or until the patient displays clinical indications of subsidence of the infection. These clinical indications of subsidence of the infection include, by way of example, a decrease in circulating levels of the virus, a decrease in the rate of patient weight loss, the complete or partial remission of the tumor, subsidance of flu-like symptoms as well as other antiviral clinical manifestations well known to those skilled in the art.

The dose of interferon postulated to be effective in humans in providing antiviral activity against a viral infection include any pharmacological non-toxic concentration or dose of IFN which is effective to elicit an antiviral response in the host. The preferred dose of interferon to be used in conjunction with the present invention is expected to vary depending on the mode of administration, the type of interferon being used, the age of the patient being treated, and the infected site (for isolated viral infection) being treated. It is expected that effective daily doses of natural HuIFN-alpha (administered I.M.) or -beta (administered I.V.) will be between $3-20\times 10^6$ $U/m^2$. Recombinant HuIFN is expected to be effective at doses of between $3-20\times 10^6$ $U/m^2$ also. Lower levels are expected to be effective considering the potentiating capacity of HS for interferon.

Others have demonstrated that it is difficult for adults to tolerate doses of 5 $Mu/m^2$ interferon or higher for any period of time without experiencing intolerable lassitude and fatigue(at page 481).[9] Others have shown that children may tolerate higher doses of interferon alone, at least for short periods of time (Ochs, et al., 1986), *J. Clin. Oncol.*, 4:883). These factors must be considered in determining dosages of the therapeutic agent, especially in treating children with viral infections.

Applicants postulate that the levels of IFN and/or TNF used in vivo in the various embodiments of the present invention may be reduced since the anticachexic agent, hydrazine sulfate (HS), is expected to potentiate antiviral activity in vivo as demonstrated in vitro. Thus, for human use, it is anticipated that preferred doses of interferon and/or TNF of the present therapeutic agents would be significantly less than those doses described in the literature for humans when used alone.[39, 9] The reduced doses of antiviral agents proposed in the present invention are postulated to avoid the attendant clinically reported side-effects of high IFN and INF treatments.

The following abbreviations are used throughout the Specification:
TNF=tumor necrosis factor
IFN=interferon
rIFN=recombinant interferon
HuIFN=human interferon
ug=microgram
U=lytic unit
HS=hydrazine sulfate
EMEM=Minimum Essential Media with Earls Salts
OD=Optical density
a=alpha
B=beta
pfu=plaque forming units
VSV=vesicular stomatitis virus
U=units
h=hour
m.o.i.=multiplicity of infection
$U/m^2$=units per body square meter
MTD=maximum tolerated dose
$Mu/m^2$=million units/meter square

DETAILED DESCRIPTION OF THE PREFERRED EMBODIMENTS

Figure 1:
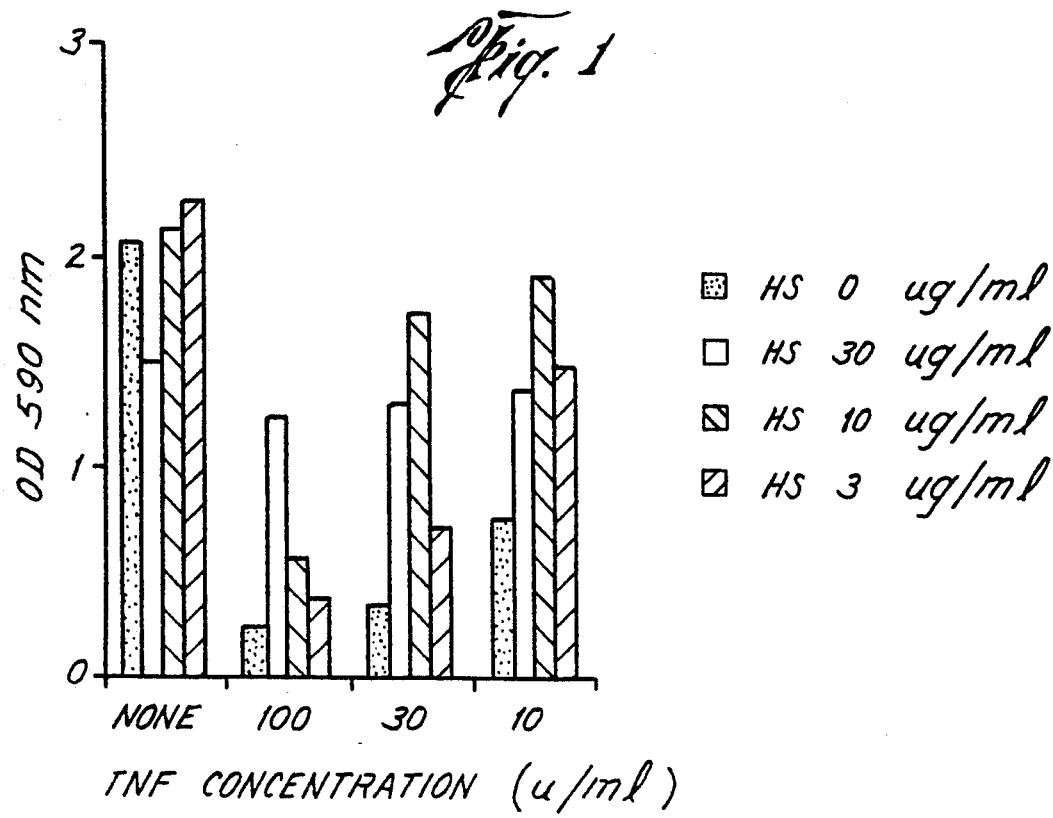
FIG. 1. Inhibition of TNF cytolytic activity by hydrazine sulfate. Mouse L-929 cells were treated with TNF in the absence or presence of hydrazine sulfate at the indicated concentrations of both for 24-36 h. Following incubation, the cells were stained and detained as before and OD 590 was determined on an automated ELISA reader.

Interferon used in some of the described studies included IFN-$B_1$ (Triton Biosciences, Palo Alto, Calif.). TNF was used, however, in most of the described studies as indicated. TNF used in the present studies was obtained from Suntory, Ltd., Tokyo, Japan. This was a recombinant human TNF (HurTNF).

Mouse L-929 cells (American Type Culture Collection Deposit #CCL 1) were prepared as described elsewhere[17] and used in the following studies. L-cells are known to be exquisitely sensitive to TNF's cytolytic activity, and therefore were particularly well suited for use in the present studies.

HEp-2 cells (American Type Culture Collection Deposit #CCL 23) were used in the following studies. These cells were grown in 96-well tissue culture plates in EMEM 10%. Upon confluency, various concentrations of TNF in EMEM 2% were placed on the cells. Twenty-four hours later and following removal of TNF, cells were challenged with vesicular stomatitis virus (VSV) at a multiplicity of infection of 0.5. Virus was harvested 24 hours later and yields were determined on L-929 cells in a modified plaque reduction assay.

The following examples are presented to describe the preferred embodiments and utilities of the present invention and are not meant to limit the present invention unless specifically indicated otherwise in the claims appended hereto.

EXAMPLE 1—HYDRAZINE SULFATE BLOCKAGE OF TNF CYTOLYSIS

The present experiment was designed to determine if hydrazine sulfate treatment of cells in vitro would block the cytolytic effect of tumor necrosis factor (TNF). The results obtained indicated that hydrazine sulfate had no significant antiviral activity itself at the concentrations used.

TNF has been shown to be cytolytic for several transformed cell lines in tissue culture, the standard assay being its cytotoxicity for actinomycin D-treated L-cells (Carswell et al., (1975); Old (1985). Therefore, Applicants tested the ability of hydrazine sulfate to block TNF cytolysis in this system. Mouse L-929 cells (American Type Culture Collection, #CCL 1) were grown to confluency in 96-well tissue culture plates (Costar, Cambridge, Mass.) in Eagle's minimal essential medium with 10% bovine serum and penicillin/streptomycin (100 units/100 ug/ml.) (EMEM 10%) at 4% $CO_2$, 37° C.

Following 24 hours incubation or upon confluence, TNF cytolytic activity was measured on L-929 cells as described in elsewhere.[17] Briefly, media was replaced with EMEM 2% containing 5 ug/ml actinomycin D in the absence or presence of various concentrations of recombinant TNF (Suntory, Tokyo, Japan). Approximately 24 hours later, cells were stained with 1% crystal violet in 20% methanol, detained with Sorenson's buffer, and optical densities determined at a wavelength of 590 nm on an automated ELIS reader.

To determine the effects of hydrazine sulfate (Sigma, St. Louis. MO) on cytolytic TNF activity, concentrations ranging from 0 to 300 ug/ml hydrazine sulfate in EMEM 2% were added to the above described assays at various times before or after TNF addition. Inhibition of TNF cytolytic activity was measured as an increase in optical density of the hydrazine sulfate/tumor necrosis factor-treated cells when compared to those treated with TNF alone. The results of these studies are demonstrated graphically in FIG. 1.

TNF cytolytic activity was measured using TNF cytotoxicity for actinomycin D-treated L-cells (Carswell et al., 1975: Old, 1985). L-cells are pretreated with actinomycin D in order to enhance the sensitivity of the cells to the cytolytic effects of TNF. The ability of hydrazine sulfate to block tumor necrosis factor cytolysis in this system was measured. As shown in FIG. 1, L-cells treated with 30, 10 or 3 ug/ml HS for 24 hours prior to exposure to 100, 30 or 10 lytic units of TNF and actinomycin D exhibited a significant decrease in cytolysis when compared to control.

These results demonstrate that hydrazine sulfate protects cells against TNF cytolysis. This data is postulated to correlate to expected effects in vivo, so as to retard tissue wasting. Applicants hypothesize this data suggests that co-administration of hydrazine sulfate with tumor necrosis factor to animals with tumorous growths or any viral condition would retard normal tissue wasting while retarding or eliminating viral replication. Tissue wasting is a condition normally attendant several viral infections and cancer. Tissue wasting in the form of host weight loss is also characteristic of virus infections caused by the human immunodeficiency virus, such as acquired immunodeficiency deficiency syndrome (AIDS) and tumor viruses, which cause cancerous conditions in humans.

EXAMPLE 2—HYDRAZINE SULFATE POTENTIATION OF TNF ANTI-VIRAL ACTIVITY

The present experiment was performed to examine the effect of hydrazine sulfate treatment on the antiviral activity of TNF, as TNF has already been shown to have an antiviral effect on some cells in culture.[1, 18]

Concentrations of hydrazine sulfate ranging from 0 to 30 ug/ml were placed on HEp-2 cells at various times relative to TNF addition. Virus yields from infected HEp-2 cells were determined by a modified plaque reduction assay on Mouse L-929 cells. Mouse L-929 cells were prepared as described in Example 1.

As shown in Table 1, a hydrazine sulfate concentration of 30 ug/ml. was demonstrated to potentiate the antiviral activity of tumor necrosis factor (TNF) several hundred fold in some cases. For example, treatment with 30 ug/ml hydrazine sulfate was shown to potentiate the antiviral activity of 100 U/ml TNF about 170 fold (173.4 fold potentiation).

TABLE 1

Modulation of TNF by Hydrazine Sulfate Potentiation of TNF antiviral activity by hydrazine sulfate

| TNF/ U/ml | HS treatment | Virus yield (log 10) | Fold inhibition Exp.[1] | Fold inhibition Obs.[2] | Potentiation |
|---|---|---|---|---|---|
| 0 | − | 5.5 | — | — | — |
| 0 | + | 5.4 | — | 1.2 | — |
| 10,000 | − | 4.5 | — | 10.4 | — |
| 10,000 | + | 2.1 | 11.6 | 2538.5 | 218.8 |
| 3000 | − | 4.6 | — | 8.5 | — |
| 3000 | + | 1.9 | 9.7 | 4400.0 | 455.5 |
| 1000 | − | 4.6 | — | 7.8 | — |
| 1000 | + | 2.0 | 9.0 | 3000.0 | 334.8 |
| 300 | − | 4.7 | — | 6.3 | — |
| 300 | + | 2.3 | 7.5 | 1833.0 | 244.4 |
| 100 | − | 4.6 | — | 7.9 | — |
| 100 | + | 2.3 | 9.1 | 1571.0 | 173.4 |

HEp-2 cells were treated with TNF at the indicated concentrations in the absence (−) or presence (+) of 30 ug/ml hydrazine sulfate. Twenty-four hours later, cells were infected with VSV (0.5 m.o.i.). Virus was harvested 24 h later and the yields determined by a modified plaque reduction assay on L-929 cells.

[1]Observed fold reduction in virus yield = $\frac{\text{virus yield in virus control}}{\text{virus yield in experiment}}$ Expected fold reduction in virus yield = observed fold reduction in experimental$_1$ + observed fold reduction in experimental$_2$.

[2]Fold potentiation = $\frac{\text{observed fold reduction}}{\text{expected fold reduction}}$

EXAMPLE 3—DIRECT EFFECTS OF HYDRAZINE SULFATE ON TUMOR NECROSIS FACTOR

The present experiment was designed to determine if hydrazine sulfate had any direct effects on TNF cytolytic activity in vitro. The possibility existed that hydrazine sulfate was acting directly on tumor necrosis factor (TNF) because of hydrazine sulfate's reducing properties. necrosis factor (TNF) (300 U/ml) with high concentrations of hydrazine sulfate (1 mg/m$^1$). Following treatment, hydrazine sulfate was dialyzed away. The treated TNF was then examined in vitro for cytolytic activity in the model described supra.

It was demonstrated in this experiment that hydrazine sulfate alone had no effect on cytolytic activity.

As shown in Table 2, hydrazine sulfate had no direct effect on TNF itself. In support of this, Applicants found that inhibition of TNF cytolysis in vitro caused by pretreatment with hydrazine sulfate could not be reversed by extensive washing of the cells. This indicated that the protective effect of hydrazine sulfate is relatively stable.

TABLE 2

| TNF (U/ml)[2] | Effect on HS on TNF[1] | |
|---|---|---|
| | Treatment[3] | OD590 nm (+ S.E.M.)[4] |
| 0 | — | 1.034 ± .38 |
| 100 | — | 0.333 ± .013 |
| 100 | Dialysis | 0.308 ± .030 |
| 100 | HS (24 H) = dialysis | 0.281 ± 0.21 |

[1]Representative of two separate experiments.
[2]Concentration expressed as cytolytic activity determined in a standard assay in actinomycin D-treated L-cells (Flick & Gifford, 1984).
[3]TNF was diluted in EMEM 2% with or without HS at a concentration of 1 mg/ml to the indicated concentrations. Twenty-four hours later, both samples were exhaustively dialyzed against phosphate-buffered saline (pH 7.4). Following dialysis, TNF standard and treated samples were for cytolytic activity.
[4]Optical density at a wavelength of 590 nm and 1:100 dilution.

EXAMPLE 4—KINETICS OF INHIBITORY EFFECTS OF HYDRAZINE SULFATE ON TUMOR NECROSIS FACTOR CYTOLYTIC ACTIVITY

This experiment was performed to determine the kinetics of the inhibitory effects of hydrazine sulfate on tumor necrosis factor's cytolytic activity in L-929 cells.

L-929 cells were prepared as described in Example 1. The L-929 were then treated with 100, 30 or 0 ug/ml of hydrazine sulfate for 16, 8, 4, 2, 1 or 0 (briefly exposed) hours. The cells were then washed three times and TNF was added in the presence of actinomycin D.

As seen in FIG. 2, maximum resistance to TNF cytolytic activity occurred between 1 and 4 hours of hydrazine sulfate pre-treatment. Thus, this study demonstrated that the minimum amount of time of hydrazine sulfate treatment required to induce the maximum amount of protection of cells from TNF cytolysis was between 1 and 4 hours. Most preferably, 1 hour is the minimum amount of time of hydrazine sulfate pre-treatment required to induce maximum protection against TNF cytolytic activity.

EXAMPLE 5—HYDRAZINE SULFATE POTENTIATION OF INTERFERON IN VITRO

Tumor necrosis factor is thought to induce its antiviral activity through interferon $B_1$[19]. Therefore, Applicants next sought to determine if hydrazine sulfate directly potentiated interferon $B_1$. HEp-2 cells were prepared as described. Concentrations of interferon $B_1$ used in this experiment were between 100 U/m$^2$–1000 U/m$^2$ together with varying concentrations of hydrazine sulfate. Concentrations of hydrazine sulfate used were between 0–30 ug/ml.

As demonstrated in Table 4, Applicants have found that hydrazine sulfate directly potentiated the antiviral activity of interferon $B_1$. It is expected that other interferons, particularly the interferon alphas, interferon gammas and other members of the interferon beta family would exhibit similar antiviral activity potentiation. However, it is not expected interferon $B_2$ would exhibit the same antiviral activity potentiation by the hydrazine sulfate, as this particular interferon is believed to function through a different mechanism. All antiviral assays were performed on HEp-2 cells. Virus yields were determined on L-929 cells. All cytolytic assays were done on L-929 cells.

At present however, it cannot be determined what the relative contributions of any intrinsic TNF antiviral activity or that of IFN-$B_1$ to the total potentiation of HS/TNF mixture comprises.

TABLE 4

HS Potentiates the Antiviral Activity of IFN-$B_1$

| IFN (U/ml)[2] | HS(ug/ml) | Virus yield (pfu/0.1 ml) | Fold reduction virus yield[1] Obs. | Fold reduction virus yield[1] Exp. | Fold potentiation |
|---|---|---|---|---|---|
| — | 0 | 40 × 10$^3$ | — | — | — |
| — | 30 | 9 × 10$^3$ | 4.4 | — | — |
| — | 10 | 29 × 10$^3$ | 1.4 | — | — |
| — | 3 | 25 × 10$^3$ | 1.6 | — | — |
| $B_1$ 1000 | 0 | 53 × 10$^3$ | 75.4 | — | — |
| $B_1$ 1000 | 30 | 26 × 10$^3$ | 1538.5 | 79.8 | 19.3 |
| $B_1$ 1000 | 10 | 52 × 10$^3$ | 769.2 | 76.8 | 10 |
| $B_1$ 1000 | 3 | 26 × 10$^3$ | 153.8 | 77 | 2 |
| $B_1$ 300 | 3 | 17 × 10$^3$ | 2.4 | — | — |
| $B_1$ 300 | 30 | 16 × 10$^3$ | 250.0 | 6.8 | 36.8 |
| $B_1$ 300 | 10 | 61 × 10$^3$ | 65.5 | 3.8 | 17.2 |
| $B_1$ 300 | 0 | 14 × 10$^3$ | 28.6 | 4 | 7.2 |
| $B_1$ 100 | 0 | 18 × 10$^3$ | 2.2 | — | — |
| $B_1$ 100 | 30 | 12 × 10$^3$ | 33.3 | 6.6 | 5.1 |
| $B_1$ 100 | 10 | 10 × 10$^3$ | 4.0 | 3.6 | 1.1 |
| $B_1$ 100 | 3 | 4 × 10$^3$ | 10.0 | 3.8 | 2.6 |

[1]Hep-2 cells (5 × 10$^3$ cells/ell) in microtiter plates were treated with IFN-B (Triton Biosciences) and/or HS at the above indicated concentrations in EMEM 2%. Twenty-four hours later supernatant fluids were decanted and the cells were infected with VSV (multiplicity of invection = 0.5). After 1 h, nonattached virus was decanted and replaced with EMEM 2%. Virus yields were determined as before.
[2]See Table 2 legend for calculation of potentiation values. Representative of three identical experiments.

EXAMPLE 6—KINETICS OF HYDRAZINE SULFATE POTENTIATION OF TNF ANTI-VIRAL ACTIVITY

This experiment was performed to determine the kinetics of the development of the potentiation of TNF antiviral activity by hydrazine sulfate. HEp-2 cells were acquired from ATCC (ATCC #CCL 23).

HEp-2 cells were treated with 30 ug/ml of hydrazine sulfate for 16, 8, 4, 2, 1 or 0 (briefly exposed) hours prior to addition of 1000 units (U) of TNF. Cells were washed free of hydrazine sulfate prior to addition of TNF.

Figure 3:
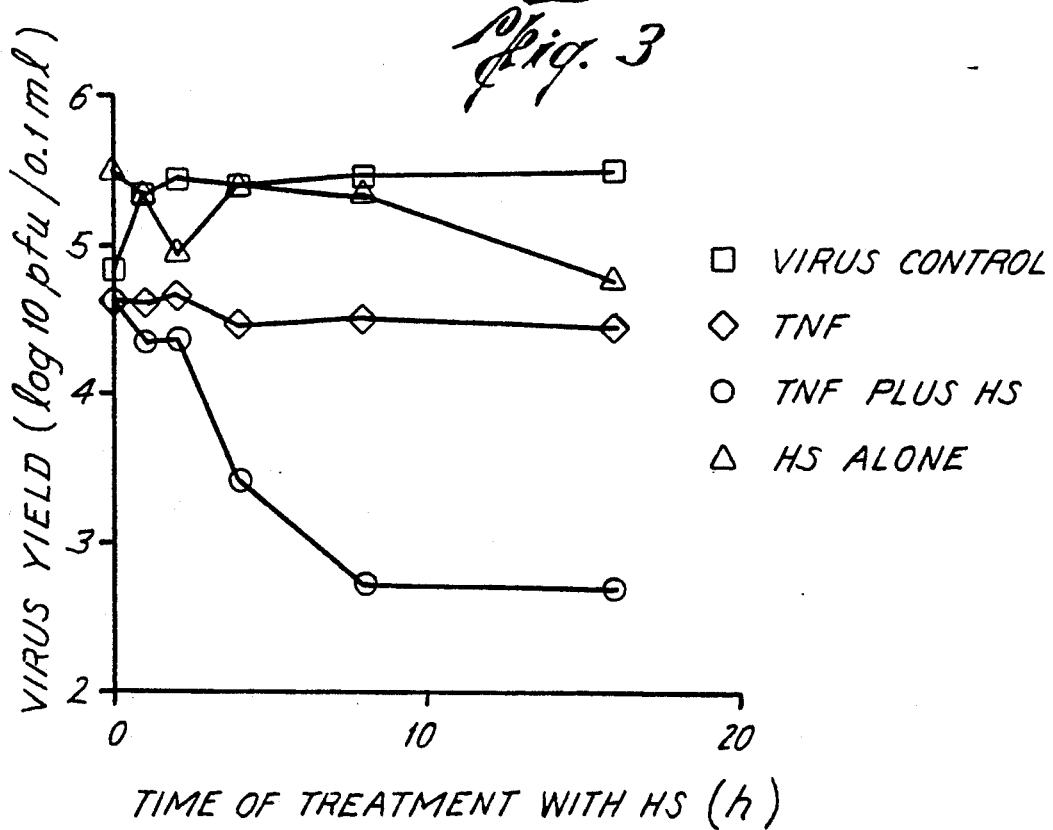
FIG. 3. Kinetics of development of the potentiation of TNF antiviral activity by hydrazine sulfate. HEp-2 cells were treated with hydrazine sulfate at the indicated concentrations and periods of time. Prior to the addition of TNF at the concentrations above, the cells were washed. Twenty-four hours later, VSV was added at a multiplicity of infection of 0.5. Virus yields were harvested 24 h later, and yields were determined by a modified plaque reduction assay on mouse L-929 cells.[16]
Figure 2A:
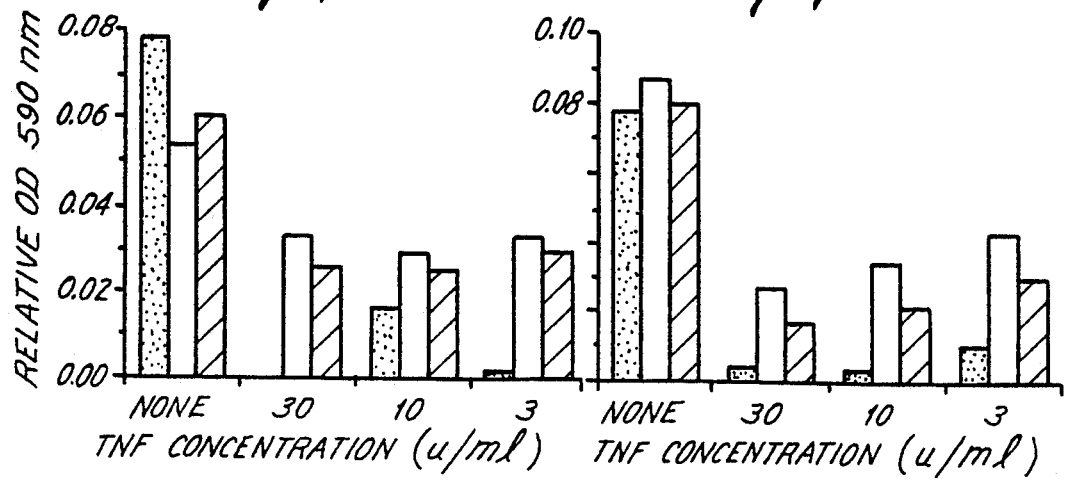
FIGS. 2A-2D. Kinetics of development of the inhibition of TNF cytolytic activity by hydrazine sulfate on mouse L-929 cells. Mouse L-929 cells were treated with the indicated concentrations of hydrazine sulfate for the indicated periods of time. Cells were then washed and TNF was added at the above concentrations in EMEM 2% with 5 ug/ml actinomycin D. Following 24 h incubation, the cells were stained and detained as before and OD 590 was determined on an automated ELISA reader.
Figure 2B:
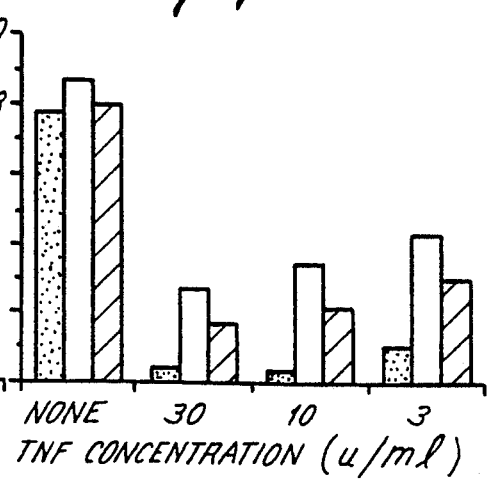
Figure 2C:
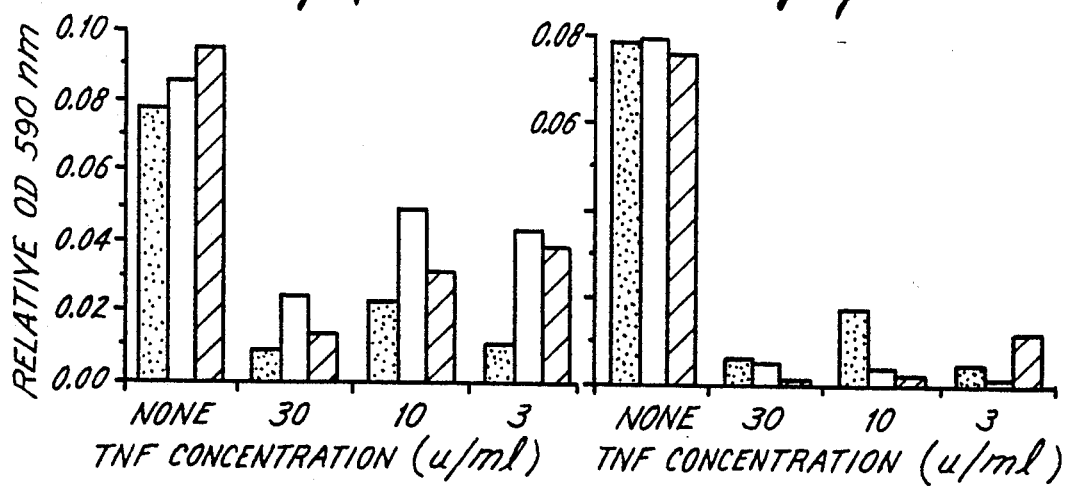
Figure 2D:
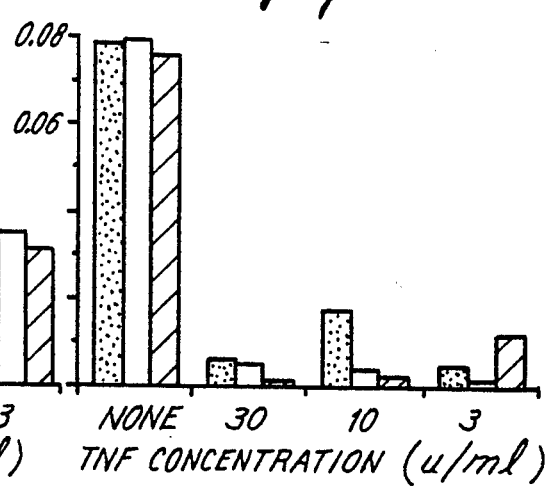

As shown in FIG. 3, there is a time-dependent effect of hydrazine sulfate on the potentiation of TNF antiviral activity. The minimum amount of time for maximum potentiation of TNF by hydrazine sulfate was between about 4 and 8 hours. This time period roughly corresponds to TNF's induction of interferon-B.

EXAMPLE 7—HYDRAZINE SULFATE INHIBITION OF TNF PRODUCTION

The following study was performed to determine if hydrazine sulfate exhibited any ability to inhibit the production of TNF by macrophages in vitro. The results presented are strictly preliminary (Applicants' unpublished results), and will require additional experimentation before conclusive results are set forth.

Human monocytes were treated with endotoxin in the absence or presence of HS. Twenty four hours later, TNF levels were measured as before. It was found that TNF levels were significantly reduced (i.e., about 50% reduction) in the presence of HS.

EXAMPLE 8—PROPOSED THERAPEUTIC USE OF TNF+HS, OR TNF+INF+HS IN THE TREATMENT OF VIRAL INFECTIONS IN VIVO

It is contemplated that the presently described therapeutic agents may be used in vivo for the treatment of viral infections. Most preferably, this treatment would be useful in the treatment of viral infections such as AIDS, ARC, and their related conditions in humans.

While Applicants expect further experimentation of particular doses in vivo will be required before the described treatment is optimized in that system, it is postulated that doses of hydrazine sulfate of between about 60 to about 250 mg per day would be effective to provide the host-protective effect, or anticachectic effects of the present invention.

The most preferred dose of HS is expected to be about 180 mg per day. Most preferably, the HS would be administered orally in the form of tablets or pills in 3 equal doses.

Where tumor necrosis factor is the antiviral agent, it is postulated that a daily dose of between about $10 \times 10^5$ $U/m^2$–$20 \times 10^5$ $U/m^2$ will provide the described antiviral protective effects of the present invention. Most preferably, it is hypothesized that a dose of about $15 \times 10^5$ $U/m^2$ will provide the antiviral activity of the invention.

Expressed as $mg/m^2$, it is postulated that about 0.04 $mg/m^2$–0.28 $mg/m^2$ TNF will be effective in providing the antiviral activity, as potentiated by the coadministration therewith of hydrazine sulfate, described in the present invention. In a more preferred embodiment, it is postulated that a daily dose of between about 0.06 $mg/m^2$ TNF will effect the potentiated antiviral activity described. Most preferably, it is hypothesized that a daily dose of 0.10 $mg/m^2$ TNF per day will produce the described effects.

Where interferon is the particular antiviral agent of the present invention, it is hypothesized that a dose of between $3$–$20 \times 10^6$ $U/m^2$ will be effective to produce the described antiviral activity in a human, when used in conjunction with between 60 mg–250 mg hydrazine sulfate per day. In a more preferred embodiment, the dose of interferon is about $8 \times 10^6$ $U/m^2$ administered with 180 mg hydrazine sulfate to provide the antiviral activity described in the present invention.

Changes may be made in the construction, operation and arrangement of the various parts, elements, steps and procedures described herein without departing from the concept and scope of the invention as defined in the following claims.

BIBLIOGRAPHY

The following documents in pertinent part are specifically incorporated herein by reference for the reasons cited in the text:

1. Kohase, et al., (1986), *Cell*, 45:659-66.
2. Wong, et al., (1986), *Nature*, 323:819-22.
3. Mustaha, et al., (1989), *Int. Arch. Allergy Appl. Immuno.*, 90:11-15.
4. Old, L. J., (1985), *Science*, 230:630-2.
5. Butler, et al., (1985a), *Nature*, 316:532-54.
6. Butler, et al., (1985b), *J. Exp. Med.*, 161:984-95.
7. Stovroff, et al., (1989), *Arc. Surg.*, 124(1):94-9.
8. Lahdevirta, et al., (1988), *Am. J. Med.*, 85(3):289-91.
9. Baron, Dianzani, Stanton and Fleischmann, eds., *In: The Interferon System, A Current Review to 1987* (1987).
10. Gold, J., (1987), *Nutr. Cancer*, 9:59-66.
11. Gold, J., (1986), *Proc. Annu. Meet. Am. Assoc. Cancer Res.*, 27:279.
12. Gold, J., (1989), *Proc. Annu. Meet. Am. Assoc. Cancer Res.*, 29:A2196.
13. Gold, J., (1975), *Oncology*, 32:1-10.
14. Sonnenfeld, et al., (1983), *Cancer Res.*, 43(10):4720-22.
15. Kim, et al., (1989), *Proc. Annu. Meet. Am. Assoc. Cancer Res.*, 30:A1618.
16. Campbell, et al., (1975), *Can. J. Microbiol.*, 21:1247-53.
17. Flick, et al., (1984), *J. Immun. Meth.*, 68:167-75.
18. Mestan, et al., (1986), *Nature*, 323:816-19.
19. Van Damme, et al., (1987), *J. Immun.*, 139:1867-72.
20. Coppenhaver, et al., (1988), *Antivir. Res.*, 9:159.
21. Carswell, et al., (1975), *Proc. Natn. Acad. Sci. USA*, 72:3666-70.
22. Clark, et al., (1988), *In: Oxygen Radicals and Tissue Injury Symposium Proceedings*, pp. 122-29.
23. Hughes, et al., (1989), *Fed. Am. Soc. Exp. Biol.*, 3(3):A636.
24. Hughes, et al., (1989), *Int. J. Immuno. Pharma.*, 11(5):501-7.
25. Gold, J., (1988), *Proc. Annu. Meet. Am. Assoc. Cancer Res.*, 29:A2196.
26. Stouroff, et al., (1989), *J. Surg. Res.*, 46(5):462-69.
27. Green, M. (1970).
28. Babich, et al. (1989), *Carcinogenesis*, 12(2):265-68.
29. Lenk, et al., (1989), *Cancer Chemother. Pharmacol.*, 24:391-2.
30. Joklik, W. K., (1986), *In: Fundamental Virology*, Chapt. 15, pp. 281-307.
31. Blalock, et al., (1981), *Biochem. Biophys. Res. Commun.*, 101:472-8.
32. Siegal, et al., (1982), *Proc. Natl. Acad. Sci. USA*, 79:4064-68.
33. Conners, T. A., (1985), *Cancer Chemotheraphy*, 7:31-56.
34. Holsti, et al. (1987), *Int. J. Radiol. Oncol. Biol. Phys.*, 13:1161-6.
35. Chlebowski, et al., (1987), *Cancer*, 59:406-10.
36. Tayek, et al., (1987), *Lancet*, Aug. 1, 1987, p. 241.
37. Silverstein, et al., (1989), *Immunopharmacology*, 17:37-43.
38. Silverstein, et al. (1988), *FASEB J.*, 2:A1173.
39. Moritz, et al. (1989), *Cancer Immunol. Immunother.*, 29:144-150.
40. Green, M., (1970), *Ann. Reo. Biochem.*, 39:701-56.
41. Chlebowski, et al., (1984), *Cancer Res.*, 44(2):857-61
42. Nizel, S., *F.A.S.E.B.*, 3(12):2379-88.

What is claimed is:

1. A method for preparing a therapeutic agent comprising:
   preparing a solution of hydrazine sulfate to form a stock solution A;
   preparing a solution of interferon to form a stock solution B; and
   diluting the stock solution A and stock solution B to a pharmaceutically acceptable final concentration to form a therapeutic agent for the treatment of viral infections.

2. The method of claim 1, wherein stock solution A comprises hydrazine sulfate at a concentration of about 25 mg/ml.

3. The method of claim 1, wherein the stock solution A is diluted to a concentration of about 1 mg/ml.

4. The method of claim 3, wherein the solution B comprises a dilution of 100 U/ml.

5. A therapeutic agent comprising a pharmaceutically acceptable concentration of an antiviral agent comprising:
   interferon; and
   a cell-protective dose of hydrazine sulfate of at least 60 mg.

6. A therapeutic agent comprising:
   a virus-inhibiting amount of interferon; and
   a cell-protecting dose of at least 60 mg of hydrazine sulfate.

7. A pharmaceutical composition containing an anti-cachexia agent and tumor nucrosis factor together in a pharmaceutically acceptable carrier or excipient, wherein the viral activity of the tumor necrosis factor is increased by the anti-cachexia agent and wherein the composition includes an amount of anti-cachexia agent sufficient to potentiate the anti-viral activity of the tumor necrosis factor.

8. The composition of claim 7 wherein the anti-cachexia agent is hydrazine sulfate.

* * * * *

UNITED STATES PATENT AND TRADEMARK OFFICE
CERTIFICATE OF CORRECTION

PATENT NO. : 5,264,208
DATED : November 23, 1993
INVENTOR(S) : Thomas K. Hughes, et al It is certified that error appears in the above-indentified patent and that said Letters Patent is hereby corrected as shown below:

In Claim 7, Column 20, line 4, change "viral activity" to --antiviral activity--.

Signed and Sealed this

Tenth Day of May, 1994

Attest:

BRUCE LEHMAN

Attesting Officer     Commissioner of Patents and Trademarks